(12) United States Patent
Mathieu et al.

(10) Patent No.: US 7,794,482 B2
(45) Date of Patent: Sep. 14, 2010

(54) DEVICE FOR OSTEOSYNTHESIS

(75) Inventors: Claude Mathieu, Bettlach (CH); Robert Frigg, Bettlach (CH); Harald Saner, Selzach (CH)

(73) Assignee: Synthes USA, LLC, West Chester, PA (US)

( * ) Notice: Subject to any disclaimer, the term of this patent is extended or adjusted under 35 U.S.C. 154(b) by 214 days.

(21) Appl. No.: 11/841,066

(22) Filed: Aug. 20, 2007

(65) Prior Publication Data

US 2008/0172094 A1 Jul. 17, 2008

Related U.S. Application Data

(63) Continuation of application No. 10/877,096, filed on Jun. 24, 2004, which is a continuation of application No. PCT/CH01/00740, filed on Dec. 24, 2001.

(51) Int. Cl.
*A61B 17/80* (2006.01)
(52) U.S. Cl. .................................... 606/290
(58) Field of Classification Search ............... 606/280, 606/70, 71, 281–299, 309
See application file for complete search history.

(56) References Cited

U.S. PATENT DOCUMENTS

| | | |
|---|---|---|
| 3,596,656 A | 8/1971 | Kaute |
| 3,993,397 A | 11/1976 | Gutshall |
| 4,029,091 A | 6/1977 | von Bezold et al. |
| 4,097,112 A | 6/1978 | Veldman et al. |
| 4,388,921 A | 6/1983 | Sutter et al. |
| 4,493,317 A | 1/1985 | Klaue |
| 5,053,036 A | 10/1991 | Perren et al. |
| 5,057,111 A | 10/1991 | Park |
| 5,085,660 A | 2/1992 | Lin |
| 5,108,399 A | 4/1992 | Eitenmuller et al. |
| 5,269,784 A | 12/1993 | Mast |
| 5,304,179 A | 4/1994 | Wagner |
| 5,352,226 A | 10/1994 | Lin |
| 5,443,467 A | 8/1995 | Biedermann et al. |
| 5,470,333 A | 11/1995 | Ray |
| 5,474,551 A | 12/1995 | Finn et al. |

(Continued)

FOREIGN PATENT DOCUMENTS

CH 672245 A5 11/1989

(Continued)

*Primary Examiner*—Eduardo C Robert
*Assistant Examiner*—Tara R George
(74) *Attorney, Agent, or Firm*—Fay Kaplun & Marcin, LLP

(57) ABSTRACT

A device for osteosynthesis that includes a fixation element having at least one through hole designed to receive a pivotable bushing for a bone screw. The through hole has a central axis and a cross-section extending orthogonally to the central axis defined by two incomplete semicircles connected to each other by at least two non-circular cut outs forming grooves in the fixation element. The device also includes at least one bushing insertable in the through hole. The bushing has top and bottom surfaces, a longitudinal axis, a central bore designed to receive a bone screw, and a peripheral outside face having at least two outwardly extending protrusions defining an axis of rotation of the bushing extending through the protrusions. A cross section of the bushing orthogonal to the longitudinal axis is shaped such that the bushing is pivotable about the axis of rotation defined by the protrusions.

35 Claims, 4 Drawing Sheets

U.S. PATENT DOCUMENTS

| | | | |
|---|---|---|---|
| 5,474,553 A | 12/1995 | Baumgart | |
| 5,486,174 A | 1/1996 | Fournet-Fayard et al. | |
| 5,501,684 A | 3/1996 | Schlapfer et al. | |
| 5,520,690 A | 5/1996 | Errico et al. | |
| 5,531,746 A | 7/1996 | Errico et al. | |
| 5,595,512 A | 1/1997 | Langdon | |
| 5,607,426 A | 3/1997 | Ralph et al. | |
| 5,607,428 A | 3/1997 | Lin | |
| 5,613,968 A | 3/1997 | Lin | |
| 5,628,740 A | 5/1997 | Mullane | |
| 5,643,265 A | 7/1997 | Errico et al. | |
| 5,669,911 A | 9/1997 | Errico et al. | |
| 5,672,176 A | 9/1997 | Biedermann et al. | |
| 5,681,319 A | 10/1997 | Biedermann et al. | |
| 5,683,465 A | 11/1997 | Shinn et al. | |
| 5,690,630 A | 11/1997 | Errico et al. | |
| 5,725,588 A | 3/1998 | Errico et al. | |
| 5,735,853 A | 4/1998 | Olerud | |
| 5,797,911 A | 8/1998 | Sherman et al. | |
| 5,797,912 A | 8/1998 | Runciman et al. | |
| 5,800,435 A | 9/1998 | Errico et al. | |
| 5,807,396 A | 9/1998 | Raveh | |
| 5,817,094 A | 10/1998 | Errico et al. | |
| 5,882,350 A | 3/1999 | Ralph et al. | |
| 5,885,286 A | 3/1999 | Sherman et al. | |
| 5,888,204 A | 3/1999 | Ralph et al. | |
| 5,891,145 A | 4/1999 | Morrison et al. | |
| 5,902,303 A | 5/1999 | Eckhof et al. | |
| 5,904,683 A | 5/1999 | Pohndorf et al. | |
| 5,938,663 A | 8/1999 | Petreto | |
| 5,954,722 A | 9/1999 | Bono | |
| 5,964,760 A | 10/1999 | Richelsoph | |
| 5,976,141 A | 11/1999 | Haag et al. | |
| 6,010,503 A | 1/2000 | Richelsoph et al. | |
| 6,017,345 A | 1/2000 | Richelsoph | |
| 6,022,350 A | 2/2000 | Ganem | |
| 6,030,389 A | 2/2000 | Wagner et al. | |
| 6,063,090 A | 5/2000 | Schlapfer | |
| 6,074,391 A | 6/2000 | Metz-Stavenhagen et al. | |
| 6,086,588 A | 7/2000 | Ameil et al. | |
| 6,113,601 A | 9/2000 | Tatar | |
| 6,132,432 A | 10/2000 | Richelsoph | |
| 6,146,383 A | 11/2000 | Studer et al. | |
| 6,176,861 B1 | 1/2001 | Bernstein et al. | |
| 6,187,005 B1 | 2/2001 | Brace et al. | |
| 6,206,882 B1 | 3/2001 | Cohen | |
| 6,235,033 B1 | 5/2001 | Brace et al. | |
| 6,280,442 B1 | 8/2001 | Barker et al. | |
| 6,315,779 B1 | 11/2001 | Morrison et al. | |
| 6,331,179 B1 | 12/2001 | Freid et al. | |
| 6,355,038 B1 | 3/2002 | Pisharodi | |
| 6,355,040 B1 | 3/2002 | Richelsoph et al. | |
| RE37,665 E | 4/2002 | Ralph et al. | |
| 6,402,756 B1 | 6/2002 | Ralph et al. | |
| 6,454,769 B2 * | 9/2002 | Wagner et al. | 606/279 |
| 6,471,705 B1 | 10/2002 | Biedermann et al. | |
| 6,485,494 B1 | 11/2002 | Haider | |
| 6,524,315 B1 | 2/2003 | Selvitelli et al. | |
| 6,565,567 B1 | 5/2003 | Haider | |
| 6,575,975 B2 | 6/2003 | Brace et al. | |
| 6,623,485 B2 | 9/2003 | Doubler et al. | |
| 6,641,586 B2 | 11/2003 | Varieur | |
| 6,660,004 B2 | 12/2003 | Barker et al. | |
| 6,663,632 B1 | 12/2003 | Frigg | |
| 6,669,697 B1 | 12/2003 | Pisharodi | |
| 6,679,883 B2 | 1/2004 | Hawkes et al. | |
| 6,689,133 B2 | 2/2004 | Morrison et al. | |
| 6,689,134 B2 | 2/2004 | Ralph et al. | |
| 6,716,214 B1 | 4/2004 | Jackson | |
| 6,723,100 B2 | 4/2004 | Biedermann et al. | |
| 6,730,093 B2 | 5/2004 | Saint Martin | |
| 6,767,351 B2 | 7/2004 | Orbay et al. | |
| 2001/0014807 A1 | 8/2001 | Wagner et al. | |
| 2001/0021851 A1 | 9/2001 | Eberlein et al. | |
| 2001/0037112 A1 | 11/2001 | Brace et al. | |
| 2002/0026193 A1 | 2/2002 | Barker et al. | |
| 2002/0045898 A1 | 4/2002 | Freid et al. | |
| 2002/0045899 A1 | 4/2002 | Errico et al. | |
| 2002/0058939 A1 | 5/2002 | Wagner et al. | |
| 2002/0143328 A1 | 10/2002 | Shluzas et al. | |
| 2002/0151900 A1 | 10/2002 | Glascott | |
| 2002/0156474 A1 | 10/2002 | Wack et al. | |
| 2003/0023243 A1 | 1/2003 | Biedermann et al. | |
| 2003/0045878 A1 | 3/2003 | Petit et al. | |
| 2003/0073996 A1 | 4/2003 | Doubler et al. | |
| 2003/0073997 A1 | 4/2003 | Doubler et al. | |
| 2003/0078583 A1 | 4/2003 | Biedermann et al. | |
| 2003/0083658 A1 | 5/2003 | Hawkes et al. | |
| 2003/0093082 A1 * | 5/2003 | Campbell et al. | 606/104 |
| 2003/0149431 A1 | 8/2003 | Varieur | |
| 2003/0153912 A1 | 8/2003 | Graf | |
| 2003/0153920 A1 | 8/2003 | Ralph et al. | |
| 2003/0158552 A1 | 8/2003 | Jeon et al. | |
| 2003/0163133 A1 | 8/2003 | Altarac et al. | |
| 2003/0187440 A1 | 10/2003 | Richelsoph et al. | |
| 2003/0187442 A1 | 10/2003 | Richelsoph et al. | |
| 2003/0199876 A1 | 10/2003 | Brace et al. | |
| 2003/0225409 A1 | 12/2003 | Freid et al. | |
| 2004/0006342 A1 | 1/2004 | Altarac et al. | |
| 2004/0015169 A1 | 1/2004 | Gause | |
| 2004/0019353 A1 | 1/2004 | Freid et al. | |
| 2004/0030339 A1 | 2/2004 | Wack et al. | |
| 2004/0068319 A1 | 4/2004 | Cordaro | |
| 2004/0087951 A1 | 5/2004 | Khalili | |
| 2004/0092930 A1 | 5/2004 | Petit et al. | |
| 2004/0092938 A1 | 5/2004 | Carli | |
| 2004/0092939 A1 | 5/2004 | Freid et al. | |
| 2004/0097933 A1 | 5/2004 | Lourdel et al. | |
| 2004/0097934 A1 | 5/2004 | Farris et al. | |
| 2004/0102781 A1 | 5/2004 | Jeon | |
| 2004/0116929 A1 | 6/2004 | Barker et al. | |
| 2004/0127897 A1 | 7/2004 | Freid et al. | |
| 2004/0127899 A1 | 7/2004 | Konieczynski et al. | |
| 2004/0127900 A1 | 7/2004 | Konieczynski et al. | |
| 2004/0127904 A1 | 7/2004 | Konieczynski et al. | |
| 2004/0127906 A1 | 7/2004 | Culbert et al. | |
| 2004/0138660 A1 | 7/2004 | Serhan | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0153073 A1 | 8/2004 | Orbay | |
| 2004/0158247 A1 | 8/2004 | Sitiso et al. | |
| 2004/0158252 A1 | 8/2004 | Prager et al. | |

FOREIGN PATENT DOCUMENTS

| | | |
|---|---|---|
| DE | 10015734 A1 | 9/2001 |
| DE | 10226496 A1 | 1/2003 |
| DE | 10227899 A1 | 3/2003 |
| EP | 0807420 A2 | 11/1997 |
| EP | 0897697 A1 | 2/1999 |
| EP | 0988833 A2 | 3/2000 |
| EP | 1153577 A1 | 11/2001 |
| EP | 1210914 A1 | 6/2002 |
| EP | 1221308 A1 | 10/2002 |
| EP | 1250892 A2 | 10/2002 |
| EP | 1306057 A2 | 5/2003 |
| EP | 1346697 A2 | 9/2003 |
| EP | 1364623 A1 | 11/2003 |
| FR | 2674118 A1 | 9/1992 |
| FR | 2744011 A1 | 8/1997 |
| FR | 2758971 A1 | 8/1998 |
| FR | 2790198 A1 | 9/2000 |
| FR | 2792185 A1 | 10/2000 |

| | | |
|---|---|---|
| JP | 5146451 | 6/1993 |
| JP | 10043202 | 2/1998 |
| JP | 11056870 | 3/1999 |
| JP | 2002/000611 | 1/2002 |
| JP | 2003/265493 | 9/2003 |
| WO | WO 95/35067 A2 | 12/1995 |
| WO | WO 96/25892 A1 | 8/1996 |
| WO | WO 99/09903 A1 | 3/1999 |
| WO | WO 99/59492 A1 | 11/1999 |
| WO | WO 03/015647 A1 | 2/2003 |
| WO | WO 03/039384 A2 | 5/2003 |
| WO | WO 03/043513 A1 | 5/2003 |
| WO | WO 03/055401 A1 | 7/2003 |
| WO | WO 03/063714 A2 | 8/2003 |
| WO | WO 03/084415 A1 | 10/2003 |
| WO | WO 03/101321 A1 | 12/2003 |

* cited by examiner

DEVICE FOR OSTEOSYNTHESIS

CROSS-REFERENCE TO RELATED APPLICATIONS

The present application is a continuation of co-pending U.S. application Ser. No. 10/877,096, filed Jun. 24, 2004, which is a continuation of the U.S. national stage application of International Patent Application No. PCT/CH01/00740, filed Dec. 24, 2001, the entire contents of both of which are expressly incorporated herein by reference.

FIELD OF THE INVENTION

The invention relates to a device for osteosynthesis, and more particularly, to a fixation device, such as a bone plate, having a polyaxial bushing and screw assembly for securing such a device to bone.

BACKGROUND OF THE INVENTION

Assemblies of the present type serve for screwing together elements such as pedicle screws or pedicle hooks in a polyaxial, rigid manner, and are used in particular in the area of the spinal column. However, these assemblies may also be employed for plating in general. Additional fields of application include use in combination with external fixators and intervertebral implants.

A device of this type is shown in U.S. Pat. No. 6,235,033, in which a screw head and the bore of the bone plate are held together by an angularly adjustable, annular bushing which is compressible and expansible by means of a slot so as to achieve an improved fastening of the screw in the plate. This known device, however, suffers from the disadvantage that the bushing used is of circular shape so that it may rotate together with the screw as the screw is screwed in, thus preventing it from becoming locked within the plate. The bushing may even turn around completely within the plate hole, so that the wrong side thereof faces upward (the inner cone tapering in the wrong direction). The present invention is intended to provide a remedy for this undesirable movement of the bushing relative to the bone plate.

It is accordingly an object of the present invention to provide a device for osteosynthesis in which the bone screws are polyaxially movable and lockable in an angularly stable manner relative to the bone plate without the need for any additional mechanical elements.

It should be emphasized that the discussion of the state of the art as set out above is merely intended to illustrate the background of the invention and does not mean that at the moment of filing the present application, or its priority application, the cited state of the art was actually published or otherwise publicly known.

SUMMARY OF THE INVENTION

According to the invention, this object is achieved by means of a device for osteosynthesis comprising a fixation element having a through hole designed to receive a multi-axially pivotal bushing for a bone screw, the through hole having a central axis and a non-circular cross-section extending orthogonally to the central axis; and a bushing insertable in said through hole, the bushing including a central bore designed to receive a bone screw, the bore having a longitudinal axis, and a peripheral outside surface configured and dimensioned to be in contact with at least a portion of the interior surface of the through hole. The bushing is configured and dimensioned to be radially compressible and radially expansible, and a cross section of the bushing extending orthogonally to the longitudinal axis of the bushing is shaped substantially the same as the cross section of the through hole such that when the bushing is inserted in the through hole, it is secured against rotation relative to its longitudinal axis while remaining pivotally adjustable relative to the fixation element.

As used herein, the term "non-circular" refers to any cross section deviating from an exactly circular shape, and refers in particular, but is not limited to, prismatic and elliptical cross sections.

One advantage achieved by the device of the present invention consists in the fact that the bushing can no longer turn about its own axis while the bone screw is screwed in. The turning of said bushing would in fact entail that no relative movement between the bushing and the screw would take place, and that the bushing would, therefore, not be expanded. Consequently, a locking of the screw would not be possible. A further advantage consists in the fact that, unlike the device disclosed in U.S. Pat. No. 6,235,033, an additional locking screw is unnecessary.

In one particular embodiment, the cross section of the through hole formed in the osteosynthetic device, which, in a preferred embodiment includes a bone plate, is polygonal, preferably hexagonal, so that said through hole has the form of a prism, preferably a hexagonal prism. In the case of the hexagonal embodiment, the bone screw may be simultaneously moved in three planes within the hexagonal through hole, making it possible to adjust and fix the screw at any desired angle. Said angle is only limited by the plate thickness and by the abutment of the bushing on the reduced cross section. It is of course also possible to use bone plates having a plurality of through holes.

In a further embodiment, the diameter of the central bore of the bushing tapers in one direction and the bore is preferably shaped in the form of a cone. This configuration permits the bushing to be spread apart by means of a corresponding counter cone. However, the bore formed in the bushing may also be realised in a circular cylindrical shape.

Preferably, the bore of the bushing is provided with an internal screw thread. This permits a locking of the bushing.

Extending orthogonally to the central axis, the cross section of the through hole formed in the osteosynthetic device, which is preferably realised as a bone plate, may also be of elliptical shape.

In a specific embodiment, the cross section of the through hole consists of two incomplete semicircles connected to one another by means of non-circular lines. In this case, the bushing is provided with two protrusions formed on its outer surface which may be inserted into the grooves formed in the through hole by the non-circular lines.

In order to be radially compressible and radially expansible, the bushing may be provided with a continuous slot preferably extending parallel to the longitudinal axis of the bushing. In an alternative embodiment, the bushing may also have a plurality of non-continuous slots preferably extending parallel to the longitudinal axis.

The surface of the bushing, preferably in the area of its peripheral, outer surface, is suitably roughened, e.g. by means of grit blasting. The through hole formed in the bone plate may correspondingly be roughened, e.g. by means of grit blasting. However, the surface of the bushing, preferably in the area of its peripheral, outside face, may also be provided with a macrostructured portion, e.g. in the form of peripheral ridges. The through hole may then be correspondingly provided with a macrostructured portion, e.g. in the form of peripheral ridges. The advantage of this configuration lies in the positive engagement between the bushing and the bone plate which is thus achievable.

In another specific embodiment, the through hole formed in the osteosynthetic device, which, in a preferred embodiment includes a bone plate, tapers towards the bottom surface and preferably also towards the top surface, thus resulting in reduced cross sections which prevent the bushing from falling out or from being pressed out. Suitably, the reduced cross section of the through hole and the compressibility of the bushing are selected adequately so that it is still possible to introduce the compressed bushing into the through hole.

The form of the peripheral outside face of the bushing is suitably convex, and preferably cylindrical.

Preferably, the osteosynthetic device—at least in the area of its through hole—and the bushing—at least in the area of its peripheral outside face—consist of different materials, preferably of materials differing from each other in hardness. The bushing may, for example, consist of a biocompatible plastic material and the osteosynthetic device (e.g. a bone plate) of a biocompatible metal. However, the bushing may also be made of metal and the device of a plastic material, preferably a reinforced plastic material. The different materials cause a plastic deformation of the surfaces and thus lead to a positive engagement.

The height of the bushing measured in the direction of its longitudinal axis should be inferior to the height of the through hole formed in the bone plate as measured in the direction of its central axis. The height of the bushing may be between 40 and 85 percent of the height of the through hole. In one specific embodiment, the height of the bushing may be between 45 and 65 percent of the height of the through hole.

The bone screws to be introduced into the bushing preferably have a conical screw head which is provided with an external screw thread. The advantage of this configuration is that the spreading and the locking of the bushing may thus be realised in a single step.

In the following, the invention and improvements of the invention will be illustrated in greater detail with reference to the partially diagrammatic representations of several embodiments. All the embodiments relate to an osteosynthetic device including a bone plate. Analogous applications for pedicle screws, pedicle hooks, external fixators, or intervertebral implants are also possible and within the scope of the present invention.

BRIEF DESCRIPTION OF THE DRAWINGS

The present invention will be understood and appreciated more fully from the following detailed description, taken in conjunction with the drawings in which.

DETAILED DESCRIPTION OF THE PREFERRED EMBODIMENTS

Figure 1:
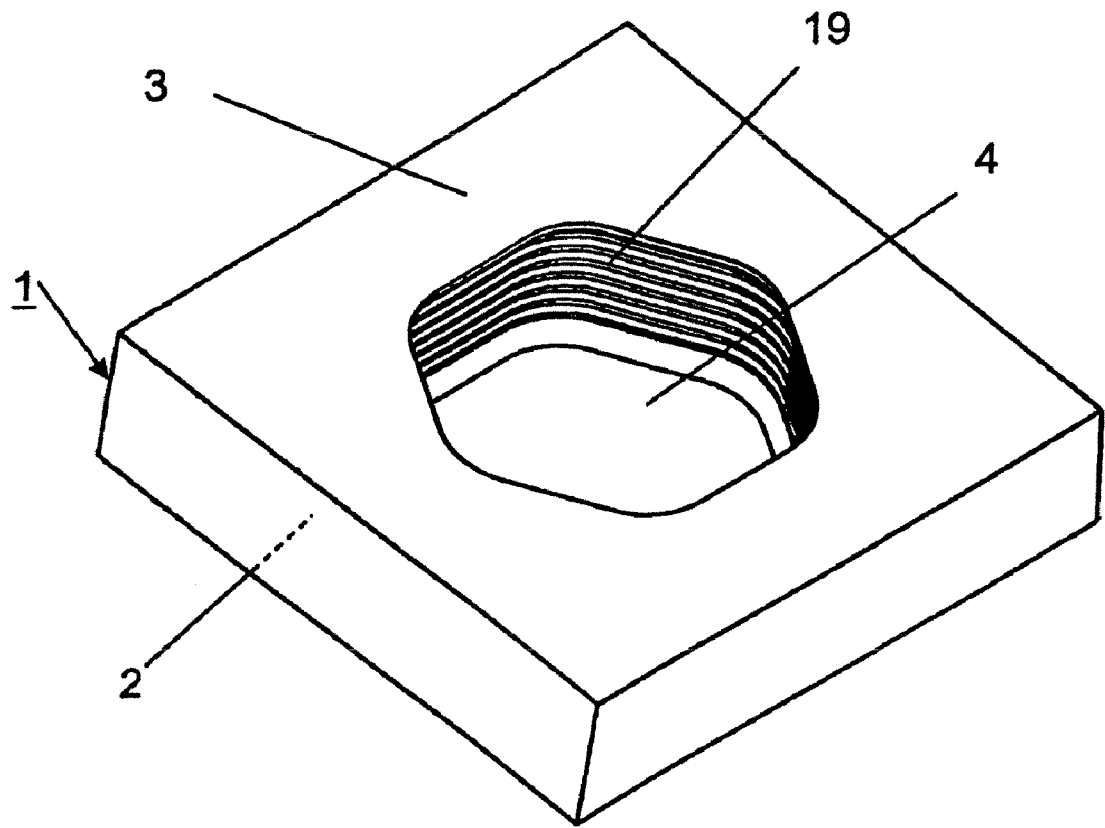
FIG. 1 is a perspective view of a fixation element according to a preferred embodiment of the present invention, wherein the fixation element is a bone plate.

The device for osteosynthesis represented in FIGS. 1 to 4 consists of a bone plate 1 including a bottom surface 2 designed to bear against the bone, a top surface 3, and a through hole 4 connecting the bottom surface 2 with the top surface 3, designed to receive a multiaxially adjustable bushing 10 for a bone screw 20 (FIG. 8), the through hole 4 having a central axis 5. The bushing 10 (FIG. 3) insertable into the through hole 4 includes a central bore 11 designed to receive the bone screw 20 (FIG. 8), the bore 11 having a longitudinal axis 12, as well as a peripheral outside face 17 designed to be in contact with the through hole 4.

The bushing 10 has a continuous slot 13 so as to be radially compressible and radially expansible. The through hole 4 of the bone plate 1 is provided, toward the bottom surface 2 and toward the top surface 3 thereof, with a reduced cross section 9 so as to prevent the bushing 10 from falling out or from being pressed out. Suitably, the reduced cross-section 9 of the through hole 4 and the compressibility of the bushing 10 are selected adequately so that it is still possible to introduce the compressed bushing 10 into the through hole 4.

Figure 2:
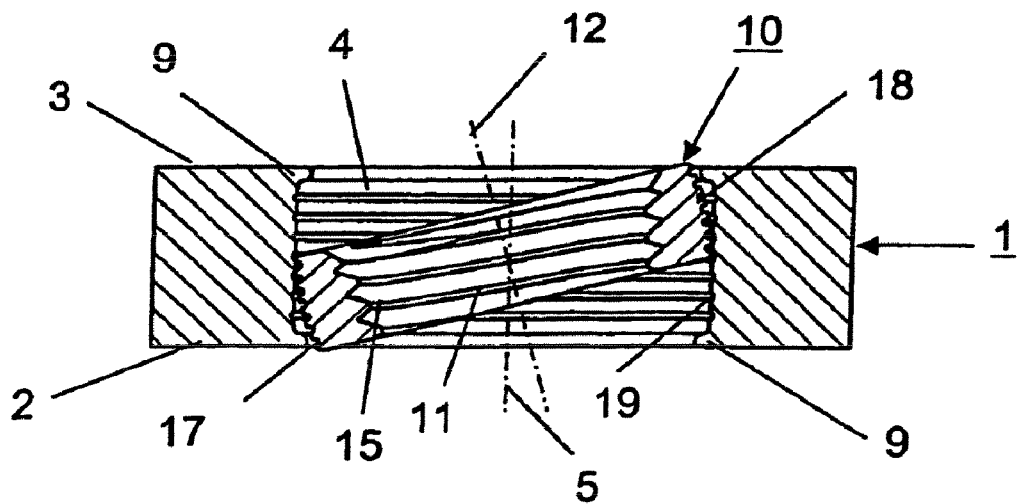
FIG. 2 is a cross section of the bone plate according to FIG. 1 with a bushing introduced therein.
Figure 3:
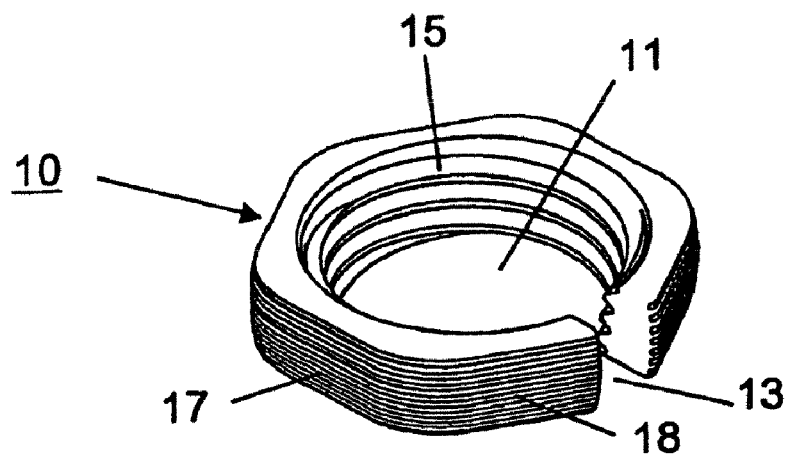
FIG. 3 is a perspective view of a bushing according to a preferred embodiment of the present invention.

As shown in FIG. 3, the surface of the bushing 10 is provided, in the area of its peripheral, outside face, with a macrostructured portion in the form of peripheral ridges 18. Correspondingly, the through hole 4 of the bone plate 1 is provided with a macrostructured portion in the form of peripheral ridges 19 (FIG. 2).

Figure 4:
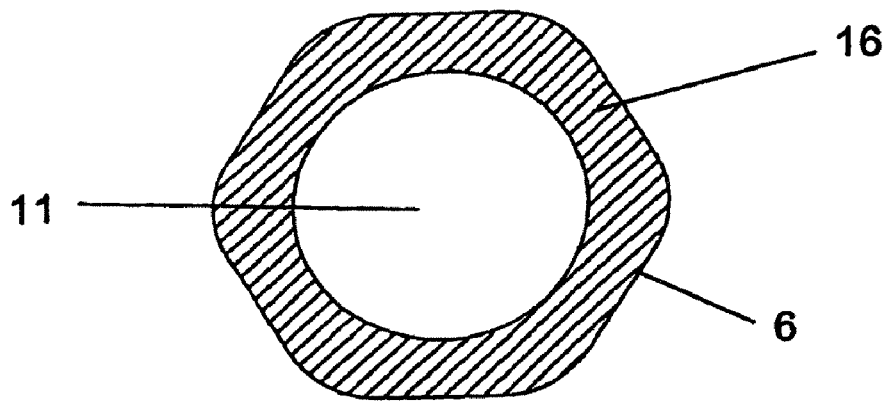
FIG. 4 is a horizontal cross section of the bushing shown in FIG. 3.

As shown in FIG. 4, the cross section 6 of the through hole 4 extending orthogonally to the central axis 5 is shaped in an approximately hexagonal, i.e. non-circular form. The cross section 16 of the bushing 10 extending orthogonally to the longitudinal axis 12 has a form corresponding substantially to that of the cross section 6 of the through hole 4 of the bone plate 1, so that the bushing 10 which is placed in the through hole 4 is rotationally stable relative to its longitudinal axis 12, while remaining adjustable within the through hole 4 as to its angular orientation relative to the bone plate 1.

As shown in FIG. 2, the diameter of the bore 11 tapers in the direction of the bottom surface 2 of the bone plate 1, so that the bore 11 has a conical shape. In addition, the bore 11 is provided with an internal screw thread 15.

Figure 5:
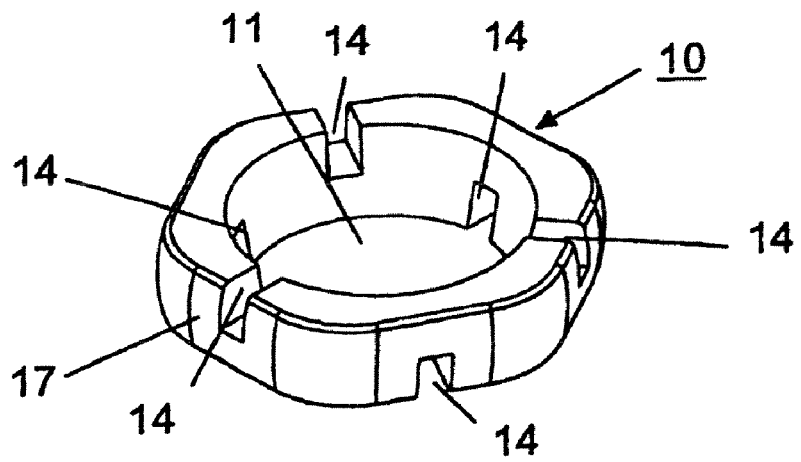
FIG. 5 is a perspective view of a bushing according to another preferred embodiment of present invention.

FIG. 5 shows another embodiment of the bushing 10 which comprises a plurality of non-continuous slots 14 extending parallel to the longitudinal axis 12. This permits the bushing 10 to be radially compressible and radially expansible without having a continuous slot.

Figure 6:
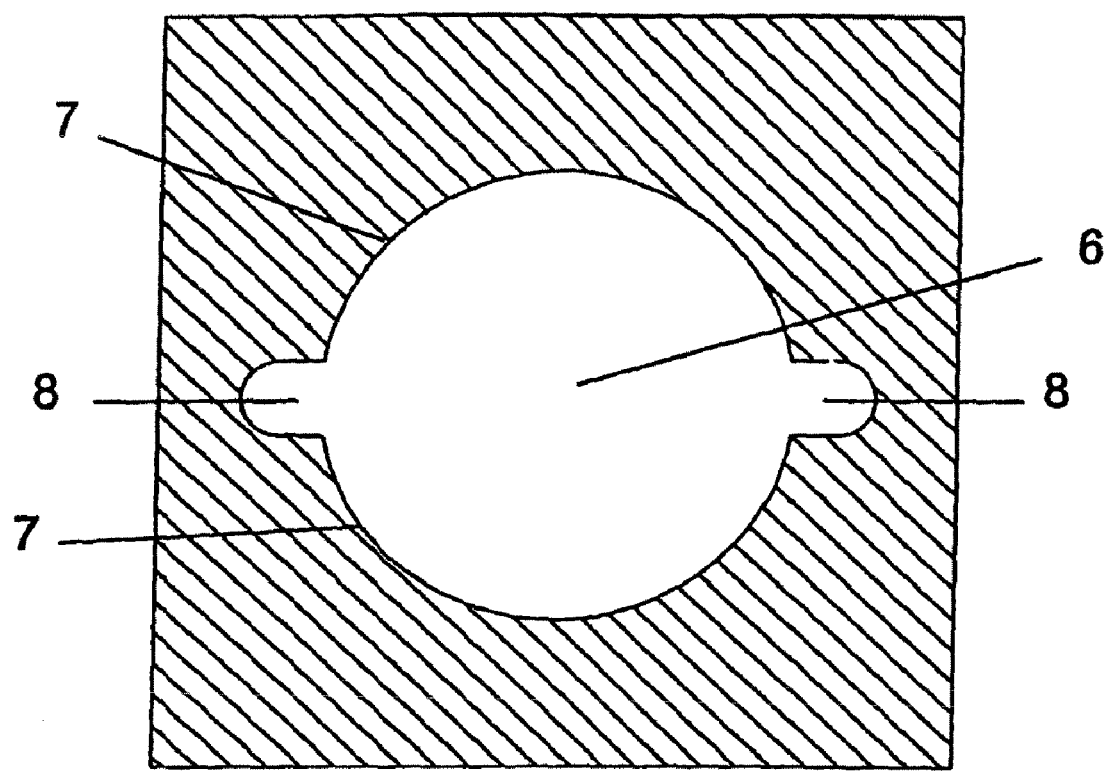
FIG. 6 is a horizontal cross section of another variation of a bone plate according to the present invention.
Figure 7:
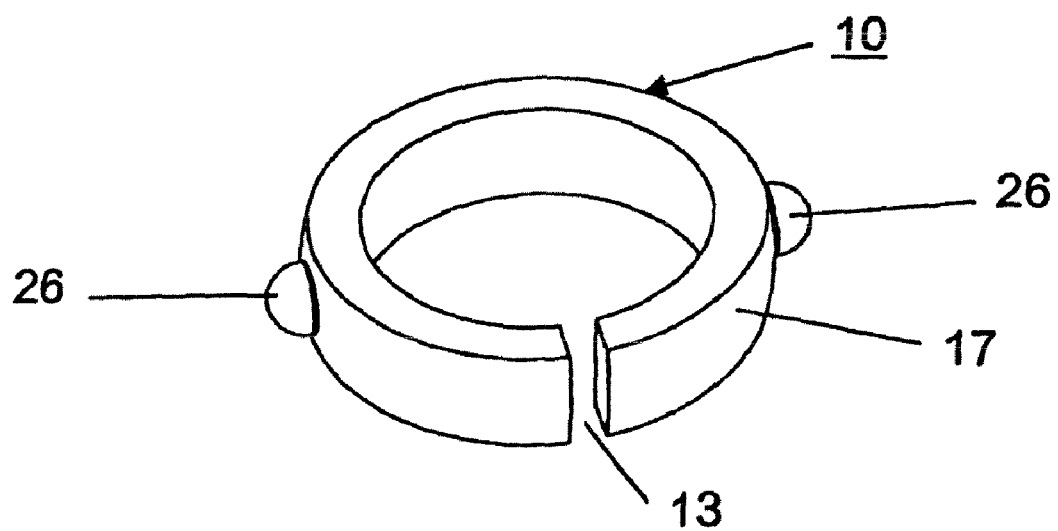
FIG. 7 is a perspective view of a bushing according to another preferred embodiment of the present invention, which mates with the bone plate according to FIG. 6.

FIGS. 6 and 7 show another embodiment of the bushing 10 and of the corresponding bone plate 1 in which the cross section 6 of the through hole 4 is defined by two incomplete semicircles 7 connected to each other by means of two non-circular lines 8. Corresponding to this, the bushing represented in FIG. 7 is shaped in the form of a ring the peripheral outside face 17 of which is spherical and which is provided with two diametrically opposed semicircular protrusions 26. The two protrusions 26 are received by the grooves formed by the non-circular lines 8 within the through hole 4 of the bone plate 1, which is equally spherical. When inserted into the bone plate, the bushing 10 is rotatable both about the two protrusions 26 and orthogonally to this axis of rotation, so that adjusting movements are possible in all directions apart from a movement in the plane of the plate (cardan joint).

Figure 8:
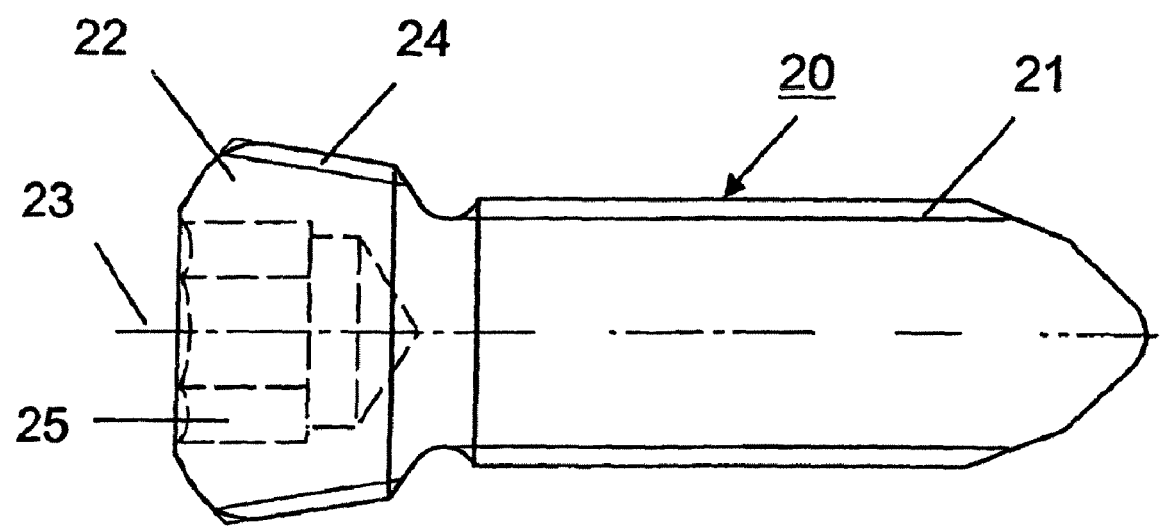
FIG. 8 is a longitudinal section of a bone screw to be used with a device for osteosynthesis according to the present invention.

The bushing 10 may receive the bone screw 20 represented in FIG. 8. The bone screw 20 has a threaded shaft 21 permitting it to be anchored within the bone, a screw axis 23, and a screw head 22 for insertion into the central bore 11 of the bushing 10, which corresponds substantially to the shape of the bore 11. The cross section of the screw head 22, which extends orthogonally to the screw axis 23, has a tapered portion proximal to the screw shaft 21, thus forming a cone. The screw head 22 is provided with an external screw thread 24 which corresponds to the internal screw thread 15 of the bushing 10. In addition, the screw head 22 is provided with a hexagon socket 15 for receiving an Allen key (not shown in the drawing).

In the following, the clinical utilization of the device for osteosynthesis will shortly be described.

The bushing 10 of the device comes preassembled in the bone plate 1 or in the jaw. It therefore does not need to be inserted by the surgeon. The bone plate with the preassembled bushings is applied to the bone. This may be done either before or after the reduction of the different bone fragments or vertebral bodies. There are three possible scenarios for placing the bone screws: a) drilling, tapping, screwing; b) drilling, screwing (using self-tapping screws); or c) screwing (using self-drilling and self-tapping screws).

It is also possible to use aiming devices or drill bushings. It is of course not suitable to use fixed aiming devices, as this would typically negate the advantage of an angularly adjustable screw, but such an aiming device may nonetheless make sense in cases in which a limitation of the range of adjustment is desirable. Drill bushings are needed in cases in which no self-drilling screws are used and a hole must be drilled prior to inserting the screw. In such cases the drill bushing serves to prevent soft-tissue injury.

There are basically two possible ways of placing a plurality of bone screws:

A) if bone reduction is done prior to the application of the plate, the screws may immediately be fastened; and B) in cases in which bone reduction is done after the application of the plate, the screws are first turned in only so far as to fix the plate on the bone; after that, the final bone reduction or correction takes place and the screws are subsequently turned in a few more angular degrees so as to become locked within the plate.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed is:

1. A device for osteosynthesis, comprising
   a fixation element having at least one through hole designed to receive a pivotable bushing for a bone screw, the through hole having a central axis defining a vertical centerline and a cross-section extending orthogonally to the vertical centerline defined by two incomplete semicircles connected to each other by at least two non-circular cut outs forming grooves in the fixation element; and
   at least one bushing insertable in the through hole, the bushing comprising:
   a top surface;
   a bottom surface;
   a longitudinal axis substantially perpendicular to the top and bottom surfaces;
   a central bore designed to receive a bone screw; and
   a peripheral outside face having at least two outwardly extending protrusions defining an axis of rotation of the bushing extending through the protrusions;
   wherein the bushing is configured and dimensioned to be radially compressible and radially expansible; and
   wherein a cross section of the bushing orthogonal to the longitudinal axis of the bushing is shaped substantially the same as the cross section of the through hole such that when the bushing is inserted into the through hole, the bushing is pivotable about the axis of rotation defined by the protrusions.

2. The device of claim 1, wherein the through hole is provided with a reduced cross-section toward a top surface and a bottom surface of the fixation element.

3. The device of claim 1, wherein the bore of the bushing tapers in one direction.

4. The device of claim 1, wherein the bore of the bushing has a conical shape.

5. The device of claim 1, wherein the bore of the bushing has a cylindrical shape.

6. The device of claim 1, wherein the bore of the bushing includes an internal thread.

7. The device of claim 1, wherein the bushing includes a continuous slot.

8. The device of claim 7, wherein the slot extends parallel to the longitudinal axis of the bushing from the top surface of the bushing to the bottom surface of the bushing.

9. The device of claim 1, wherein the through hole includes a reduced cross section proximal a bottom surface of the fixation element and proximal a top surface of the fixation element to prevent dislodgment of the bushing.

10. The device of claim 9, wherein the reduced cross section of the through hole and the compressibility of the bushing are configured and adapted to permit insertion of the compressible bushing into the through hole.

11. The device of claim 1, wherein the peripheral, outer surface of the bushing is convex relative to the longitudinal axis of the bore in the bearing.

12. The device of claim 1, wherein an inner surface of the through hole is convex relative to the central axis of the through hole.

13. The device of claim 1, wherein an inner surface of the through hole and the peripheral outer face of the bushing have complementary shapes.

14. The device of claim 1, wherein the bushing has a height measured in the direction of its longitudinal axis, and the through hole of the fixation element has a height measured in the direction of its central axis, and the height of the bushing is less than the height of the through hole.

15. The device of claim 1, further comprising a bone screw having a threaded shaft for anchoring within the bone, a longitudinal screw axis, and a screw head configured and dimensioned for insertion into the central bore of the bushing.

16. The device of claim 15, wherein the screw head corresponds substantially to the central bore of the bushing.

17. The device of claim 15, wherein a cross section of the screw head orthogonal to the longitudinal screw axis conically tapers towards the threaded shaft.

18. The device of claim 15, wherein the screw head includes external threads.

19. The device of claim 1, wherein the fixation element is a bone plate having a bottom surface designed to bear against bone, and a top surface, and the through hole extends from the bottom surface to the top surface.

20. The device of claim 1, wherein the two outwardly extending protrusions are diametrically opposed.

21. The device of claim 1, wherein the bushing has a second axis of rotation orthogonal to the axis of rotation defined by the protrusions.

22. The device of claim 21, wherein the bushing is pivotable about the axis of rotation defined by the protrusions and the second axis of rotation when the bushing is inserted into the through hole.

23. The device of claim 1, further comprising a plurality of through holes and a plurality of bushings inserted into the plurality of through holes.

24. A bone plate, comprising
a bottom surface for contacting bone, a top surface, and at least one through hole extending from the bottom surface to the top surface, the through hole having a central axis defining a vertical centerline and a cross-section extending orthogonally to the vertical centerline defined by two incomplete semicircles connected to each other by at least two non-circular cut outs forming grooves in the bone plate; and
at least one bushing insertable in the through hole, the bushing comprising:
a top surface;
a bottom surface;
a longitudinal axis substantially perpendicular to the top and bottom surfaces of the bushing;
a central bore designed to receive a bone screw; and
a peripheral outside face having at least two outwardly extending protrusions defining an axis of rotation of the bushing extending through the protrusions;
wherein the bushing is configured and dimensioned to be radially compressible and radially expansible; and
wherein a cross section of the bushing orthogonal to the longitudinal axis of the bushing is shaped substantially the same as the cross section of the through hole such that when the bushing is inserted into the through hole, the bushing is pivotable about the axis of rotation defined by the protrusions.

25. The bone plate of claim 24, wherein the bushing has at least one continuous slot.

26. The bone plate of claim 25, wherein the slot extends parallel to the longitudinal axis of the bushing from the top surface of the bushing to the bottom surface of the bushing.

27. The bone plate of claim 24, wherein the bushing has a height measured in the direction of its longitudinal axis from the top surface to the bottom surface of the bushing, and the through hole of the bone plate has a height measured in the direction of its central axis from the top surface to the bottom surface of the bone plate, and the height of the bushing is less than the height of the through hole.

28. The bone plate of claim 24, wherein the bushing has a second axis of rotation orthogonal to the axis of rotation defined by the protrusions.

29. The bone plate of claim 28, wherein the bushing is pivotable about the axis of rotation defined by the protrusions and the second axis of rotation when the bearing is inserted into the through hole.

30. The bone plate of claim 24, further comprising a plurality of through holes and a plurality of bushings inserted into the plurality of through holes.

31. A device for osteosynthesis, comprising
a bone plate having at least one aperture designed to receive a bushing for a bone screw, the aperture having a vertical centerline line and an arcuate internal surface centered on the vertical centerline and a cross-section extending orthogonally to the vertical centerline having first and second slots extending on opposite sides of an entrance of the aperture; and
at least one bushing formed of a tubular body sized for placement in the at least one aperture and having an axial centerline and a transverse centerline, the bushing comprising:
an outer annular wall having an outer surface,
a top planar surface;
a bottom planar surface;
an internally threaded bore;
first and second transversely-aligned protrusions extending horizontally outwardly from opposite sides of the outer surface of the outer annular wall; and
a continuous slot in the tubular body extending from the top planar surface to the bottom planar surface and from the internally threaded bore to the outer surface of the outer annular wall; and
wherein the outer surface of the outer annular wall is convex relative to the axial centerline so as to have an outwardly-bowed arcuate shape complementary to the arcuate internal surface of the aperture.

32. The device of claim 31, wherein the first and second transversely-aligned protrusions define a pivot axis extending through the bushing and the centers of the transversely-aligned protrusions.

33. The device of claim 32, wherein the bushing has a second pivot axis orthogonal to the pivot axis defined by the transversely-aligned protrusions.

34. The device of claim 33, wherein the bushing is pivotable about the pivot axis defined by the transversely-aligned protrusions and the second pivot axis when the bushing is inserted into the aperture.

35. The device of claim 31, further comprising a plurality of apertures and a plurality of bushings inserted into the plurality of apertures.

* * * * *